US00PP31686P3

(12) United States Plant Patent
Maillard et al.

(10) Patent No.: US PP31,686 P3
(45) Date of Patent: Apr. 21, 2020

(54) CHERRY TREE NAMED 'BICOLAM'

(50) Latin Name: ***Prunus avium* (L.) L.**
Varietal Denomination: BICOLAM

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/350,459

(22) Filed: Nov. 20, 2018

(65) Prior Publication Data

US 2019/0159380 P1 May 23, 2019

(30) Foreign Application Priority Data

Nov. 23, 2017 (QZ) ..... PBR 2017/3041

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181, 180
CPC ..... A01H 5/08; A01H 5/085; A01H 5/0827; A01H 5/0216; A01H 6/74; A01H 6/7445
See application file for complete search history.

*Primary Examiner* — June Hwu
(74) *Attorney, Agent, or Firm* — Birch, Stewart, Kolasch & Birch, LLP

(57) ABSTRACT

A new and distinct variety of cherry tree denominated 'BICOLAM' has fruits that ripen medium in the season, said variety being self-fertile and resistant to cracking, allowing a high production of fruits with large size and light to dark red or two-colored fruit skin, depending on maturity stage, firm, and with a good flavor and eating quality; the fruit is further characterized by its good handling and storage qualities.

3 Drawing Sheets

Latin name of the genus and species of the plant claimed: *Prunus avium* (L.) L.

Variety denomination: 'BICOLAM'.

This application claims priority of Community plant variety right No. 2017/3041 filed on Nov. 23, 2017 (Nov. 23, 2017) which is hereby incorporated by reference in its entirety.

The new variety named 'BICOLAM' is also known as 6N.18-2.48.14CE-ASF1607. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and the year of selection. Then before being named 'BICOLAM', the provisional reference of this cherry tree variety was 6N.18-2.48.14CE, corresponding to the tree 48 located in line 18-2 of the parcel 6N and selected during the year 2014. The letters "CE" are related to the first letters of the type of tree in French (CE for "CErise", that means "cherry"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'BICOLAM', the clone reference was 'ASF1607'.

BACKGROUND OF THE NEW VARIETY

Field of the Invention

In the field of plant genetics, we conduct an extensive and continuing plant-breeding program including the organization and reproduction of orchard trees, among which peaches, nectarines, apricots, apples, and cherries are exemplary.

It was against this background of our activities that the present variety of cherry tree was originated and reproduced by us in our experimental orchard located near Elne, Pyrénées Orientales, France.

ORIGIN OF THE VARIETY

The present invention relates to a new a distinct variety of cherry tree *Prunus avium* L. which has been given the variety denomination 'BICOLAM'. This tree produces fruits with a long shelf life without alteration both on the trees after growth completion and after harvesting, very good eating quality with a cream pink colored flesh, and for fresh market during June in the Pyrénées Orientales department, France.

Contrast is made to 'FIRELAM' cherry tree (U.S. Plant Pat. No. 25,564), 'ROSALOLAM' cherry tree (U.S. Plant Pat. No. 29,252), 'BURLAT' cherry tree (not patented), and 'FOLFER' (not patented) cherry tree for reliable description. 'BICOLAM' is a promising candidate for commercial success in that it produces very attractive fruits having a long shelf life.

The present new variety of cherry tree (*Prunus avium* L.) was developed by us in our experimental orchard located in France. 'BICOLAM' cherry tree originated in a cultivated area of the South of France, in the Pyrénées-Orientales department where it was also tested. This zone also called Roussillon is subject to a Mediterranean climate. The winter is generally sweet, in relative comparison with other areas of production, regarding the total amount of cold hours lower than 7° C. (Celsius) that varies from 600 hours to 1200 hours, depending on the year. The summer is hot and dry, that is to say the total amount of sunshine hours is an average of 2400 hours to 2800 hours per year. The prevailing wind is called "Tramontane": it dries the air and clear the sky from clouds, but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen, and the summer is dry with a few thunderstorms.

The 'BICOLAM' variety resulted from an open pollination of the cherry tree variety named 'FIRELAM' (U.S. Plant Pat. No. 25,564) which was used as the seed parent. Thus, the pollen parent is unknown.

The 'BICOLAM' variety was obtained by hybridizing and propagated by grafting on a 'Maxma14' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

Every known type of grafting adapted to the cherry tree may be performed on the new tree. Especially, the type of grafting will depend on the grafting period and the propagation mode which is used by the nursery owner. Thus, the grafting period may be micrografting at any moment of the year if the grafting is performed in greenhouse, dormant eye shield budding in August or September, growing eye shield budding in June or July.

Compared to its female parent, a red cherry tree named 'FIRELAM' (U.S. Plant Pat. No. 25,564), the new variety 'BICOLAM' is considered as a two-colored cherry tree or red cherry tree, depending on the maturity stage.

Regarding the flowering period, the flowers of the new variety 'BICOLAM' bloom generally slightly later than the flowers of the 'FIRELAM' variety. Thus, generally, the flowers of 'BICOLAM' bloom 2 to 3 days after the flowers of 'FIRELAM'.

Moreover, the new variety 'BICOLAM' is considered self-fertile whereas the 'FIRELAM' variety is not self-fertile and needs to be pollinated by another variety.

Compared to the cherry tree named 'ROSALOLAM' (U.S. Plant Pat. No. 29,252), the new variety 'BICOLAM' shows a similar maturity period. However, the new variety is self-fertile whereas the 'ROSALOLAM' variety is not, such as the 'FIRELAM' variety.

Compared to the fruits produced by the cherry variety named 'BURLAT' (not patented), that show a weight of about 7.5 to 8 grams, the 'BICOLAM' variety produces fruits that are heavier, with a weight of approximately 13 grams and more, and the fruits of 'BICOLAM' have a bigger size. The 'BURLAT' variety is considered to be sensitive to cracking whereas the new variety 'BICOLAM' is resistant to cracking.

Compared to 'FOLFER' cherry tree, which is considered to be sensitive to cracking whereas the new variety 'BICOLAM' is resistant to cracking. Also, the ripening period for the fruits produced by the variety 'FOLFER' is earlier than the ripening period of the new variety 'BICOLAM'. More particularly, the first fruits of 'FOLFER' usually ripen approximately 10 days before the first fruits of the variety 'BICOLAM'.

SUMMARY OF THE NEW VARIETY

The new variety 'BICOLAM' produces fruits of important size, firm, with a semi-sweet flavor, low acidity, and a red color of skin, sometimes a two-colored skin, depending on the maturity stage of the fruits. Indeed, because of their long lasting on trees, the fruits of the new variety 'BICOLAM' may either be harvested early while fruits have a two-colored skin, or later with a very luminous light red color covering the whole surface of the fruits, or even later to get dark red fruits. Consequently, depending on the harvesting date, the fruit skin color may evolve from a light red color to a darker red color. The blooming period is medium for the variety, generally at the end of March or at the beginning of April. The maturity period is considered medium, and generally begins at the end of May or early in June, in the South of France. However, it was observed that its date of blooming and maturity seem to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
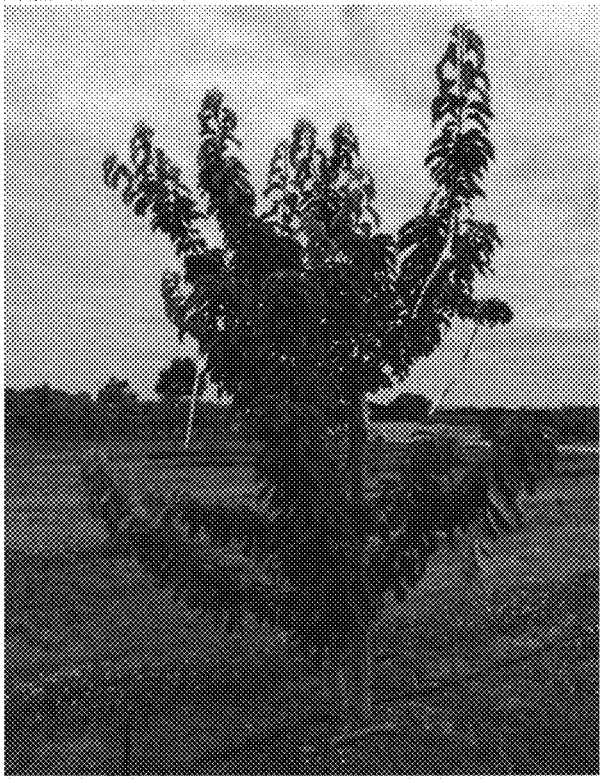
FIG. 1 is a color photograph which shows a view of a tree of the new variety in orchard at ripening time.
Figure 2:
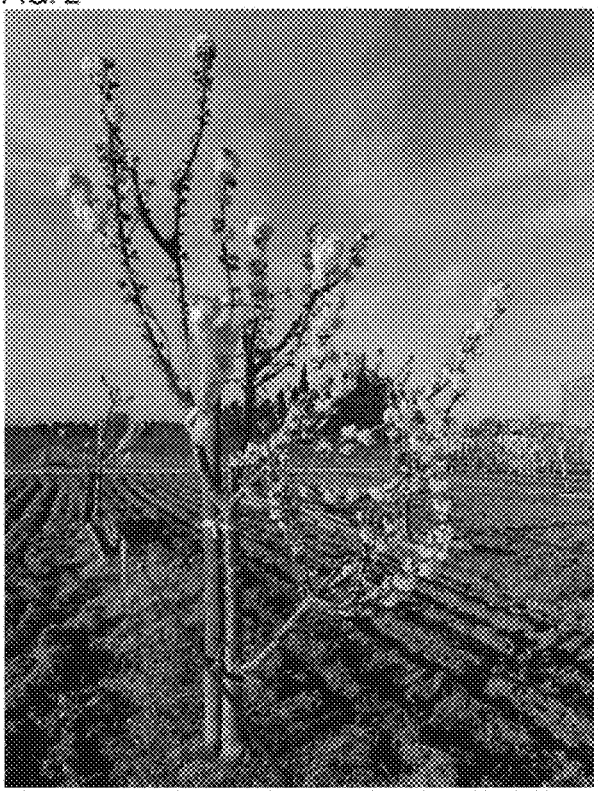
FIG. 2 is a color photograph which shows a view of a tree of the new variety in orchard at blossoming time.
Figure 3:
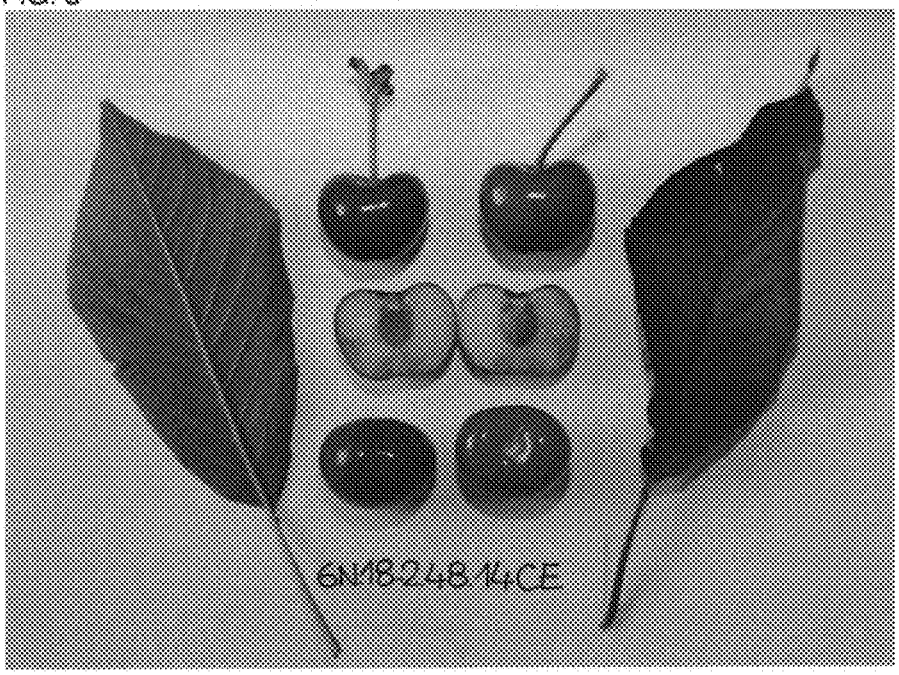
FIG. 3 is a color photograph which shows the upper and lower sides of leaves, five whole fruits of the new variety with dark red skin, one of these having been cut in a half, with the stone being left in one of the halves, for depicting the fruit flesh, the stone, and the stone cavity of the new variety, also referenced as '6N.18-2.48.14CE' on FIG. 3.
Figure 4:
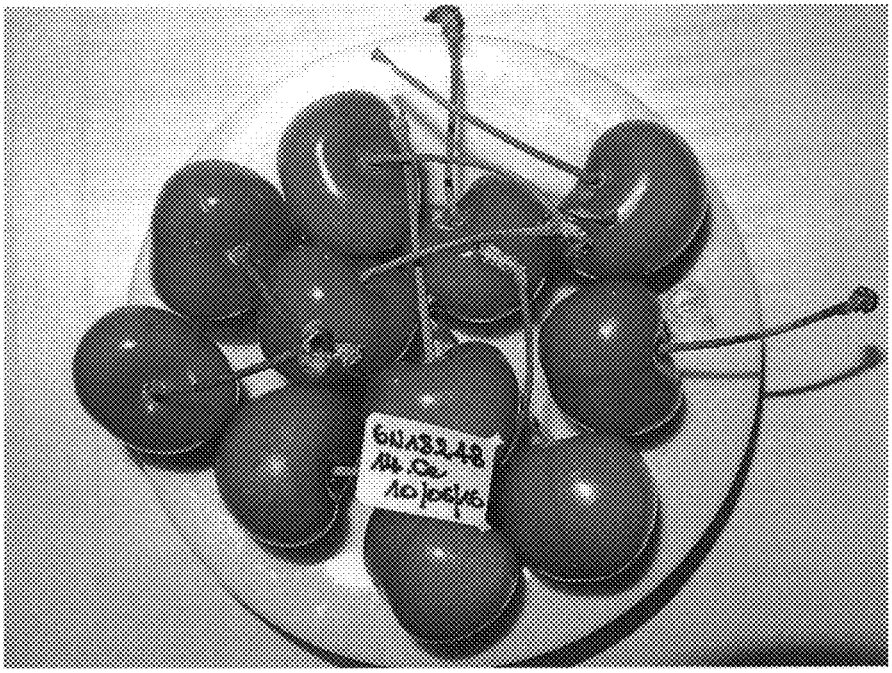
FIGS. 4 and 5 are color photographs that shows a close view of typical fruits of the new variety 'BICOLAM', also referenced as '6N.18-2.48.14CE' on FIG. 4, at ripening time, the fruit color being lighter that the fruit skin color visible on FIG. 3 and sometimes with light red on a yellow background.
Figure 5:
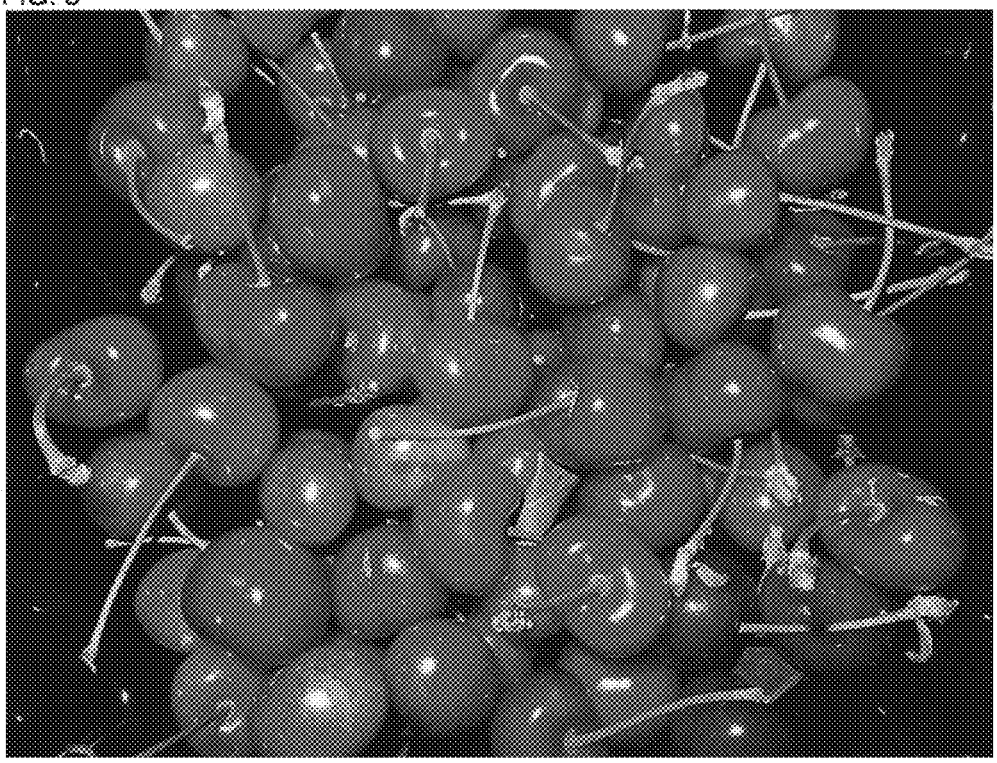
Figure 6:
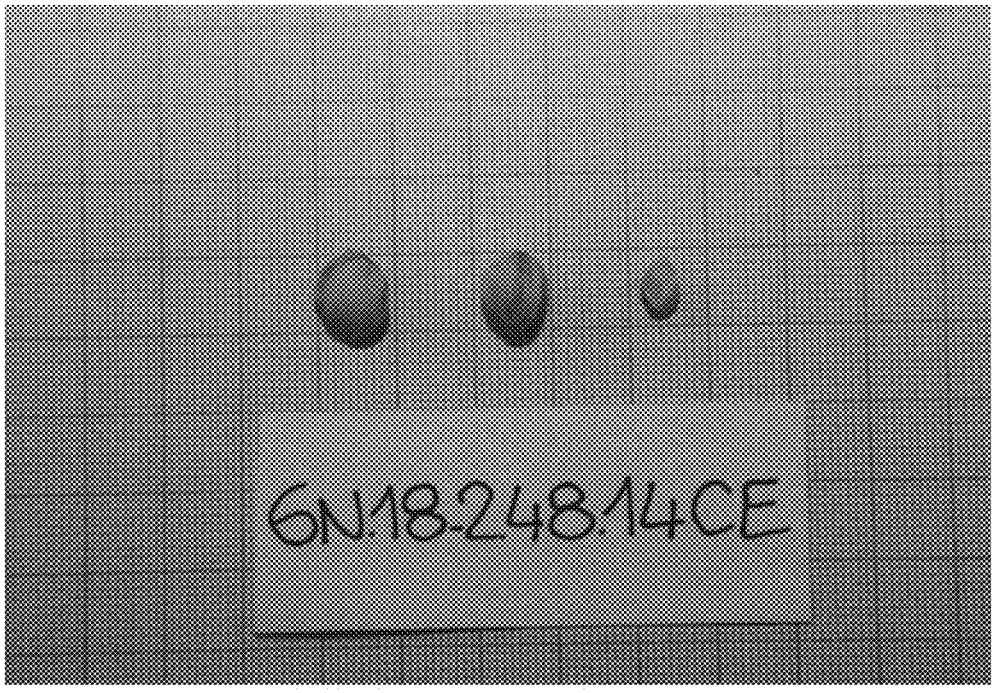
FIG. 6 is a color photograph showing different views of the stone and the kernel of the stone of the new variety, also referenced as '6N.18-2.48.14CE' on FIG. 6.

The enclosed photographs show plants in their fourth growing season, except for the tree and trunk illustrated on FIG. 1, that have been observed in their sixth growing season and the tree with flowers at blossoming illustrated on FIG. 2, that have been observed in their fifth growing season.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of cherry tree, its flowers, foliage and fruit, as based on observations of specimens grown near Elne, South of France, with color in accordance with The R.H.S. (Royal Horticultural Society) Colour Chart (Fourth Edition) provided by The Royal Horticultural Society of Great Britain.

The trees, flowers and fruits may vary in slight detail due to variations in soil type, cultural practices and climatic conditions.

The main characteristics of this new variety of sweet cherry are a big fruit size with a light to dark red or two-colored skin depending on the maturity stage. The color of fruit flesh is cream to pink. The fruit is firm.

The time of beginning of flowering is medium and the ripening period is also considered medium.

DETAILED DESCRIPTION

Referring more specifically to the pomological details of this new and distinct variety of cherry tree, the following has been observed on trees on their fourth growing season (third year of production) for leaves, fruits and stones, on trees on their fifth growing season (fourth year of production) for flowers and on trees on their sixth growing season (fifth year of production) for trees and trunks, under the ecological conditions prevailing at the orchards located near the town of Elne, Pyrénées-Orientales department, France.

All observations have been done on rootstock cultivar. The rootstock was a 'MAXMA14' tree. All major color code designations are by reference to The R.H.S. (Royal Horticultural Society) Colour Chart 2001 (Fourth Edition) provided by The Royal Horticultural Society of Great Britain.

Tree: Generally. The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical, and the diameter is limited to 1 meter.

*Size*.—Medium to high as compared to other commercial sweet cherry cultivars. The tree size the first year was approximately 2.50 meters. The tree was pruned during each following dormant season to a height of approximately 2.50 meters. Current season's shoots growth could reach 0.60 to 0.80 meters. So, the tree size from the second year (second and next years) reached a final height of 3.10 to 3.30 meters. The mature branches have been pruned to a length of 30.0 centimeters in order to place nets on the trees.

*Spread*.—Approximately 2.0 meters with a cylindrical shape. The whole orchard was oriented to a central leader organization, with tree lines spaced of 4.0 meters and trees spaced of 1 meter in a same tree line.

*Vigor*.—Medium, tree growth reaching 0.60 to 0.80 meters the first growing season.

*Productivity*.—Good productivity, every year. The new variety produces adequate fruit set annually on a regular basis. The number of the fruit set varies with the prevailing climatic conditions and cultivar practices employed during the bloom period and is therefore not distinctive of the present variety.

*Bearer*.—Very regular and quantitative. The extinction of the clusters of May improves the size and firmness of the fruit.

*Form*.—Semi-spread.

*Hardiness*.—Medium in all stone fruit growing areas of France and especially where the chilling requirement is between 350 and 1200 hours. No injury with temperatures as low as −12° C. in winter. Good resistance to late frosts. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017 and 1017 hours in 2017-2018, showed a good behavior of the tree in all cases.

Trunk:

*Size*.—Medium. Approximately 90.0 to 94.0 millimeters above 20.0 centimeters from ground, on $6^{th}$ growing season.

*Bark texture*.—Rough with reliefs due to the lenticels.

*Lenticels*.—High number of lenticels. The number of lenticels reaches approximately 10 lenticels per 10 $cm^2$. At the $6^{th}$ growing season, lenticels are 1.5 to 2.5 millimeters in height and 7.0 to 12.0 millimeters in width.

*Lenticels color*.—Color of lenticels is light orange (RHS GREYED ORANGE 164 A).

*Bark color*.—Brown (RHS BROWN 200 B).

Branches:

*Size*.—Medium for the branches at the $6^{th}$ growing season.

*Diameter*.—Average diameter of 12.0 to 18.0 millimeters.

*Surface texture*.—Smooth with small lenticels, round to slightly stretched. The number of lenticels reaches 20 lenticels per 10 $cm^2$. The lenticels are 1.0 to 2.0 millimeters in height and approximately 1.5 to 2.0 millimeters in width. The color of lenticels is considered beige (RHS GREYED ORANGE 64 C to RHS GREYED ORANGE 64 D). Wood that is several years old has furrowed appearance.

*Color*.—Mature branches show a brown color (RHS GREY BROWN N199 A).

*Tree branching strength*.—Medium.

Current season shoots:

*Size*.—Medium for the new growth, between 60.0 and 80.0 centimeters.

*Diameter*.—Considered medium. Average diameter of about 5.0 to 7.0 millimeters.

*Surface texture*.—Smooth.

*Crotch angles*.—Primary branches are considered variable, but the crotch angles are generally 45 degrees from the vertical axis. This particular characteristic is not considered distinctive of the variety, however.

*Internode*.—Considered short. Generally from 18.0 millimeters to 23.0 millimeters length and 24.0 to 28.0 millimeters on two years old branches.

*Color*.—Current season shoots are considered light brown to slightly green (RHS GREY BROWN 199 A or RHS GREY BROWN N 199 D) on their lower face and brown slightly darker (RHS GREY BROWN 199 A or RHS GREY BROWN N 199 A) on their upper face.

Leaves:

*Size*.—Medium for the species. Leaf measurements have been taken from vigorous, upright, current-season growth at approximately mid-shoot. The ratio leaf length/leaf width is approximately 2.14.

*Length*.—From 122.0 to 145.75 millimeters without leaf petiole.
*Width*.—From 58.0 to 68.0 millimeters.
*Leaf form in cross view*.—Concave.
*Leaf form*.—Entire to rhomboid.
*Apex*.—Acuminate.
*Leaf base*.—Cuneiform.
*Margins*.—Undulated and dentate or crenate.
*Thickness*.—Medium.
*Uniformity*.—Leaves are generally identical.

Leaf color:
*Upper leaf surface*.—Dark green (RHS YELLOW GREEN 147 A).
*Lower surface*.—A lighter green than the upper leaf surface (RHS YELLOW GREEN 147 B).
*Leaf texture*.—Smooth, without pubescence (glabrous). The lower surface is also smooth without pubescence.
*Leaf venation*.—Pinnately veined.

Mid-vein:
*Color*.—The mid-vein or midrib is green (RHS YELLOW GREEN 146 D or RHS YELLOW GREEN N 144 A) and the color may evolve with maturity.
*Thickness*.—Approximately 2.0 millimeters.

Lateral veins:
*Color*.—The lateral veins are considered a light green (RHS YELLOW GREEN 144 A or RHS YELLOW GREEN 144 B).

Leaf petioles:
*Size*.—Considered medium to long.
*Length*.—About 42.0 to 52.0 millimeters.
*Diameter*.—About 1.75 to 2.0 millimeters.
*Shape*.—Ribbed.
*Color*.—Upper surface greenish (RHS YELLOW GREEN 152 A) and sometimes pale red (RHS GREYED PURPLE N 186 C). Lower surface light green (RHS YELLOW GREEN 145 A).
*Ratio blade length/petiole length*.—More or less 2.75 to 3.0.

Leaf glands:
*Size*.—Considered medium. Their length is about 2.0 to 2.25 millimeters. Their width is between 1.0 and 1.5 millimeters.
*Number*.—Generally 2.
*Type*.—Round.
*Margins*.—Smooth and regular.
*Position*.—Alternated on the upper part of the petiole.
*Color*.—On young leaves, the leaf glands are considered red (RHS RED 46 A). The leaf gland color evolves with maturity and, on older leaves, the leaf glands are colored in a brown red (RHS GREYED ORANGE 172 A).

Leaf stipules:
*Generally*.—No leaf stipules were observed.

Flowers:

Flower buds:
*Generally*.—At pre-floral stage of development, the floral bunches are make up with 3 to 4 floral buds having a conic shape with a round tip. Their form is evolving until blooming, with variables dimensions. Then, just before blooming, floral buds have a diameter of about 8.0 to 10.0 millimeters and are approximately 15.0 to 18.0 millimeters long. The distribution of the flower buds is considered homogenous on the trees.
*Color*.—This characteristic is dependent upon the proximity to bloom. At pre-floral stage of development, the bottom of the flowers buds, or calyx, or flower receptacle, is of green or light green color at the upper surface (RHS YELLOW GREEN 153 B or RHS YELLOW GREEN 153 C or RHS YELLOW GREEN N 144 A or RHS YELLOW GREEN 151 A). The lower surface of the calyx is considered green (RHS YELLOW GREEN 145 A or RHS YELLOW GREEN 145 B) to brown (RHS GREYED ORANGE 175 A or RHS GREYED RED 178 A). Above the calyx, the corolla, formed by petals, is generally pure white (RHS WHITE 155 D) on both upper and lower surfaces.
*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.
*Date of bloom*.—Generally late March or at the beginning of April. Last four blooms took place respectively from Apr. 2 until Apr. 9, 2015, then from Apr. 2 until Apr. 11, 2016, then from Mar. 20 until Mar. 28, 2017 and then from Apr. 2 until Apr. 12, 2018.
*Blooming time*.—Considered medium relative comparison to other commercial cherry cultivars grown in the Pyrénées-Orientales department, France. The date of full bloom is observed at the middle of the blooming period. The date of bloom varies slightly with climatic conditions and cultural practices.
*Blooming period*.—Average 8-10 days. This characteristic varies slightly with the prevailing climatic conditions.
*Flower type*.—The variety is considered to have a showy type of flowers (rosette).
*Flower size*.—Considered medium. Average diameter between 34.0 and 37.0 millimeters when totally opened.
*Bloom quantity*.—Considered abundant or very abundant, approximately 250 to 300 flowers per meter.
*Flower bud frequency*.—Generally 3 to 4 flower buds appear per node.

Petal:
*Size*.—Considered medium for the species.
*Length*.—Generally between 15.0 and 17.0 millimeters.
*Width*.—Generally between 16.0 and 17.0 millimeters.
*Petal form*.—Round.
*Petal count*.—Nearly always 5.
*Petal texture*.—Both petal surfaces have a smooth texture.
*Petal margins*.—Slightly undulate.
*Petal color*.—Pure white color (RHS WHITE 155 D) on both surfaces.
*Fragrance*.—Soft.
*Arrangements of petals*.—Slightly overlapping.

Petal claw:
*Form*.—The claw is considered to have a narrow form.
*Length*.—Approximately 1.0 to 1.5 millimeters.

*Width*.—Approximately 1.5 millimeters.

*Color*.—Same color as the petal's color (RHS WHITE 155 D).

Petal apex:

*Generally*.—The petal apices are generally wide dome shaped.

Flower pedicel:

*Length*.—Considered medium to long and having an average length of approximately 19.0 to 23.0 millimeters.

*Diameter*.—Average 1.5 millimeters.

*Color*.—Green (RHS YELLOW GREEN 144 B to RHS YELLOW GREEN 144 C).

Calyx:

*Internal surface texture*.—Smooth.

*Color*.—The inner surface of the calyx, or flower receptacle, is of green or light green color (RHS YELLOW GREEN N 144 A to RHS YELLOW GREEN 151 A or RHS YELLOW GREEN 153). The outer surface of the calyx is considered green or green to brown (RHS YELLOW GREEN 145 B to RHS GREYED ORANGE 175 A).

Sepals:

*Surface texture*.—The outer and inner surfaces of the sepals have a smooth texture.

*Size*.—Usually considered medium.

*Length*.—Approximately 6.0 to 7.0 millimeters.

*Width*.—Approximately 4.0 to 5.0 millimeters.

*Shape*.—Conic with a round-shape on top.

*Color*.—The upper surface is green (RHS YELLOW GREEN 144 A to RHS YELLOW GREEN 144 B) or brown (RHS GREYED ORANGE 175 A). The lower surface of the sepals is considered green (RHS YELLOW GREEN 144 C).

*Number of sepals*.—Generally 5, no overlapping.

*Sepal apex*.—Round

*Margin descriptors*.—Smooth.

Stamens:

*Average number of stamens per flower*.—Between 28 and 32 stamens per flower.

*Stamen*.—size compared to petals. The size of stamen is smaller than the size of petals.

Anthers:

*Length*.—Medium.

*Form*.—Cardioid.

*Color*.—Yellow color (RHS YELLOW 11 A). The color evolves with flowering.

*Pollen production*.—Pollen is abundant and has a yellow color (RHS YELLOW 11 A or RHS YELLOW 11 B) that varies with maturity. The fertility has been checked and the 'BICOLAM' variety is self-fertile (or self pollinating).

Filaments:

*Size*.—Variable in length, approximately between 11.0 and 13.0 millimeters in length, generally smaller than pistil's length.

*Color*.—Considered as white (RHS WHITE 155 B or RHS WHITE 155 C).

Pistil:

*Number*.—Usually 1.

*Length*.—Approximately from 16.0 to 17.0 millimeters including the ovary, that is longer than stamens length.

*Color*.—Considered very pale green (RHS YELLOW GREEN 145 C). The color is evolving with flowering.

*Surface texture*.—Glabrous.

*Pubescence*.—Absent.

*Stigma*.—Approximately 1.0 millimeter in diameter, with an elliptic shape and a yellowish color (RHS YELLOW GREEN N 144 A).

*Ovary*.—Approximately 3.0 to 4.0 millimeters in height. The diameter of the ovary is about 2.0 to 3.0 millimeters. The color is considered green (RHS YELLOW GREEN 144 A to RHS YELLOW GREEN 144 B).

Type of reproduction: Pollination.

Pollinator: BICOLAM is a self-fertile or self-pollinating variety. So, it doesn't need any pollinator.

Fruits:

*Maturity when described*.—Firm at maturity.

*Date of last picking*.—Last known picking times carry on from May 22 to May 27, 2014, then May 1 to May 8, 2015, then from May 8 to May 14, 2016, then from Apr. 22 to Apr. 28, 2017 and then from May 31 to Jun. 8, 2018.

*Ripening period*.—Grouped maturity, approximately 6 to 9 days.

Size:

*Generally*.—Considered large to very large, with a homogeneous size between them.

*Average cheek diameter*.—About 24.0 to 27.0 millimeters.

*Average axial diameter*.—About 25.0 to 27.0 millimeters.

*Typical weight*.—Considered big. Generally about 12.0 grams, sometimes 13.0 grams or more. This characteristic is highly dependent upon the prevailing cultural practices, and therefore is not particularly distinctive of the variety.

Fruit form:

*Generally*.—Reniform.

*Fruit suture*.—Slightly marked and homogenous from the base to the apex, with a flared shape.

*Suture color*.—Generally slightly darker than the skin color and considered purple red (RHS GREYED PURPLE 187 A).

Ventral surface:

*Form*.—Smooth.

*Apex*.—Round. Slightly in depression.

*Base*.—Slightly in depression.

*Stem cavity*.—Average depth of the stem cavity is about 4.0 to 6.0 millimeters. Average width is about 6.0 to 7.0 millimeters, with a flared shape.

Fruit skin:

*Thickness*.—Considered thin, and tenacious to the flesh depending on stage of maturity.

*Tenacity*.—Tenacious to flesh and strong.

*Texture*.—Smooth and glabrous.

*Taste*.—Sweet.

*Tendency to crack*.—None.

Color:

*Blush color*.—The color of the fruit is considered two colored or light to dark red, depending on the maturity stage. When the fruits are mature, the fruit skin is colored on 90-95% of its surface in purple red (RHS GREYED PURPLE 187 A to RHS GREYED PURPLE 187 B) on red background (RHS RED 53 A).

*Fruit stem*.—Considered long, approximately 42.0 to 50.0 millimeters.

*Diameter*.—Approximately 1.2 to 1.5 millimeters.

*Color*.—Light green (RHS YELLOW GREEN 144 A).

*Description*.—Resistant and flexible, no splitting when removed.

*Lenticels*.—None.

Flesh:

*Ripens*.—Homogenous, slow and regular.

*Texture*.—Very crunchy, luscious, juicy.

*Fibers*.—No fibers.

*Firmness*.—Considered firm.

*Aroma*.—Pronounced aroma.

*Eating quality*.—Very good, very sweet, aromatic.

*Flavor*.—Semi-sweet, very sugared, aromatic. Low acidic level. Juicy and aromatic.

*Juice*.—Large amount, very juicy.

*Brix*.—Approximately 15.7 to 18.0 degrees, varies slightly with amount of fruit per tree and climatic conditions.

*Color of juice*.—From a cream to pink color (RHS RED 37 A) at ripeness.

*Color of flesh*.—Pink cream (RHS ORANGE 29 C or RHS ORANGE 26 C or RHS ORANGE 26 D), with a slightly red pigmentation at ripeness.

Stone:

*Type*.—Semi-freestone or semi-clingstone at fruits picking.

*Size*.—Medium for the variety.

*Length*.—Average 9.0 to 10.0 millimeters.

*Width*.—Average width 9.0 to 10.0 millimeters.

*Diameter*.—Average diameter 8.0 to 9.0 millimeters.

*Form*.—Round.

*Base*.—Generally round to slightly oblique.

*Apex*.—Round.

*Stone cavity*.—Medium with a form and dimensions corresponding to the stone's dimensions.

Stone surface:

*Surface texture*.—Smooth.

*Ridges*.—None, smooth.

*Tendency to split*.—Splitting is absent.

Ventral edge:

*Width*.—Very shallow, more or less 0.5 millimeter.

Dorsal edge:

*Shape*.—Fully grooved.

*Stone color*.—The color of the dry stone is light beige (RHS GREYED YELLOW 161 C or RHS GREYED YELLOW 161 D).

Kernel:

*Size*.—Medium.

*Length*.—About 7.0 to 9.0 millimeters.

*Width*.—About 4.0 to 6.0 millimeters.

*Thickness*.—About 3.0 to 6.0 millimeters.

*Form*.—Obovoid to round.

*Pellicle*.—Not pubescent, smooth.

*Color*.—The kernel skin is light beige (RHS GREYED YELLOW 162 B or RHS GREYED YELLOW 162 C). The kernel and its embryo (almond) are mature at the time of fruit maturity.

*Almond*.—The almond has a bitter taste and a white color (RHS WHITE 155 A).

Use: Dessert. Fresh products.

*Market*.—Local and long distance. On the tree fruits can stay 10 days while keeping good gustative qualities. The lifetime after picking is also good.

Keeping quality: Good behavior on trees, allowing either a harvest of the fruits of this variety as a bicolor cherry, or to harvest the fruits later as a red cherry. Also, held well for 30 days in cold storage at 2° C. and maintained good appearance and eating quality.

Shipping quality: Good, showed minimal bruising or scarring during picking, packing and shipping trials.

Plant/fruit disease resistance/susceptibility: specific tests were run and 'BICOLAM' variety seems to be low sensitive to observed pathologies, to rupture and to conservation pathologies.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

The invention claimed is:

1. A new and distinct variety of cherry tree, substantially as illustrated and described, characterized by its medium ripening, its self fertility, its high production, its resistance to cracking, its attractive fruits and especially by its large to very large size, its light to dark red or two colored fruit skin depending on the maturity stage, its firmness, good flavor and eating quality; the fruit is further characterized by its good handling and storage qualities.

* * * * *